United States Patent [19]
Richard et al.

[11] Patent Number: 5,935,518
[45] Date of Patent: Aug. 10, 1999

[54] SWIMMING POOL TREATMENT

[75] Inventors: Wanda G. Richard; Nimai C. De, both of Rochester, N.Y.

[73] Assignee: Bausch & Lomb Incorporated, Rochester, N.Y.

[21] Appl. No.: 08/763,820

[22] Filed: Dec. 11, 1996

Related U.S. Application Data

[60] Provisional application No. 60/010,770, Jan. 29, 1996.

[51] Int. Cl.$^6$ .............................. C02F 1/50; A01N 33/02
[52] U.S. Cl. ............................... 422/28; 422/6; 504/158; 514/635; 514/674; 210/764
[58] Field of Search .................... 422/6, 16, 28; 504/158, 160; 514/635, 674; 210/764

[56] References Cited

U.S. PATENT DOCUMENTS

| | | |
|---|---|---|
| 2,393,293 | 1/1946 | Corley . |
| 3,428,576 | 2/1969 | Dickinson et al. ..................... 260/2 |
| 4,014,676 | 3/1977 | Carter et al. . |
| 4,304,590 | 12/1981 | Grade et al. ........................ 504/158 |
| 4,608,289 | 8/1986 | McIntosh ............................ 428/95 |
| 4,758,595 | 7/1988 | Ogunbiyi et al. ................... 514/635 |
| 4,836,986 | 6/1989 | Ogunbiyi et al. ................... 422/28 |
| 5,449,658 | 9/1995 | Unhoch et al. ..................... 504/151 |
| 5,489,588 | 2/1996 | Hsu ................................... 514/237.8 |
| 5,668,084 | 9/1997 | Unhoch et al. . |

FOREIGN PATENT DOCUMENTS

| | | | |
|---|---|---|---|
| 158800 | 2/1983 | German Dem. Rep. ......... | C23F 7/00 |
| 1407258 | 9/1975 | United Kingdom . | |
| 1464005 | 2/1977 | United Kingdom . | |
| 2298575 | 11/1996 | United Kingdom ........... | A01N 25/00 |

OTHER PUBLICATIONS

F. Devinsky et al, "Cut–off Effect in Antimicrobial Activity and in Membrane Perturbation Efficacy of the Homologous Series of N,N–Dimethylalkylamine Oxides", J. Pharm. Pharmacol., vol 42 pages 790–794 1990.

Patent Abstracts of Japan, vol. 014, No. 458 (C–0766), Oct. 3, 1990 & JP 02 184609 A (Sanyo Chem Ind Ltd), Jul. 19, 1990, see abstract.

Patent Abstracts of Japan, vol. 095, No. 009, Oct. 31, 1995 & JP 07 150194 A (Mitsubishi Materials Corp), Jun. 13, 1995, see abstract.

Fuller, A.T. "Antibacterial Action and Chemical Constitution in Long–chain Aliphatic Bases, " Biochemical J., pp. 545–558, 1942.

Hueck, Hendrik J. et al. "Bacteriostatic, Fungistatic, and Algistatic Activity of Fatty Nitrogen Compounds," Applied Microbiol., pp.308–319, May 1996.

*Primary Examiner*—Elizabeth McKane
*Attorney, Agent, or Firm*—Chris P. Konkol

[57] ABSTRACT

This invention relates to the treatment of pool surfaces and equipment with antimicrobial solutions which contain straight chain alkylamine compounds alone or in combination with additional bactericidal agents, such as biguanides.

13 Claims, 5 Drawing Sheets

SWIMMING POOL TREATMENT

This application claims the benefit of U.S. Provisional Application No(s).: 60/010,770 Jan. 29, 1996.

BACKGROUND OF THE INVENTION

1. Field of the Invention

The instant invention is related to the field of baths (such as in for example a swimming pool, a hot tub, a spa, a sauna, a whirlpool, a Jacuzzi, etc.) and maintenance and treatment of the water, associated facilities and equipment using antimicrobial agents, and the compounds therein.

2. Description of the Prior Art

A healthy and attractive pool should ideally contain crystal clear water that is free of any biological pathogens. The physical structures that are associated with a pool (such as the physical pool walls, drains and plumbing, pumps, deck, assorted instruments used to clean and maintain the pool, etc.) must also be free from biological pathogens as well. Traditional technology for treating and maintaining the quality of pool water is well known in the art and is described in, for example, Ralph L. Johnson, YMCA Pool Operations Manual, (Human Kinetics Publishers, Inc., Champaign, Ill., 1987), and David G. Thomas, Swimming Pool Operators Handbook, National Swimming Pool Foundation, Washington D. C., 1972).

Clarification of water in pools is usually accomplished via consecutive dilution using continuously flowing filtered water. While water that is turbid may be perfectly healthy for use, it is not usually attractive to most potential swimmers. Sand filters and diatomaceous earth filters employing both perpetual and temporary media have been the traditional choice for filtration of large commercial pools. Cartridge filtration, first developed for private pool use, has now been applied to larger pools as well. Because of the demands for high flow rate, it is impractical to attempt to filter out microscopic biological pathogens. Clarification is designed to remove larger particulate matter from suspension thereby reducing turbidity, and is generally not designed for removing biological pathogens. Biological pathogens are removed using antimicrobials. Commonly used antimicrobials for pools are chlorine, and the related halogens bromine and iodine. When chlorine gas is injected into pool water, the resulting chemical reaction produces hypochlorous acid, and hydrochloric acid. The hydrochloric acid, which is not a useful product and reduces pool pH, must be neutralized by the addition of soda ash. Hypochlorous acid is a strong bactericide and oxidizer, however it undergoes further ionization into hydrogen ion and hypochlorite ion, in a pH dependent fashion. Hypochlorite ion is not an effective bactericidal agent, and not a good oxidizer. Higher pH tends to increase the ionization of hydrochloric acid, and thus reduce the effectiveness of the bactericidal treatment. However, chlorine and related halogens are limited in the breadth and scope of antimicrobial action, and are limited to being present in solution with effective concentrations limited by concerns of the irritation and discomfort to swimmers by high concentrations.

The combination of warm water, high pH, and sunlight provide ideal conditions for algae (for example red, green, brown, black, or blue-black algae) to grow and become attached to the sides and bottoms of the pool. If uncontrolled, algae growth in an outdoor pool can spread very rapidly. While algae are generally not responsible for disease, it is desirable to eliminate them because they deplete chlorine, cause turbidity and slimy surfaces in and outside of the pool, and can cause foul odors which make the pool uninviting, and may also create safety hazards. Generally, preventive maintenance is seen as the best solution to algae problems. Usually the maintenance of a free chlorine residual above 1.0 ppm, and a pH range of 7.4 to 7.6 greatly reduces the chance of algae flowering, but it does not eliminate the problem. Prevention of algae growth is usually not difficult, but removing algae from a pool after it has gained a foothold can be extremely difficult, and normal procedures of treatment with halides are ineffective.

Standard treatments are inefficient in stopping the establishment of algae, at lower concentrations that are not irritating to swimmers, and are generally directed to inhibiting the flowering of algae. The most effective and practical method of treatment once the algae have attached, is to drain the pool and physically clean the growth off with a dilute muriatic acid or hypochlorite solution. It would be very useful to have new disinfecting agents for pools that could be used to effectively inhibit algae growth and/or eliminate bacteria in pools, that is both easy to use and will have a minimal impact on the delicate balance of water quality in the pool. Highly effective, non-toxic antimicrobial agents which could inhibit the growth of bacteria, fungi, and yeast, especially on surfaces would be highly desireable.

Most preventative measures attempt to limit the growth of algae by treating water. The earliest algicide to be used extensively in natural waters was copper sulfate, but the toxicity makes them inappropriate for use in pools. High concentrations can cause skin rashes and turn hair green, and may cause a milky precipitate to form in highly alkaline or sulfur containing water. Some mercury compounds (phenylmercuric acid) have been found to be algaecidal, and were previously used, but the cumulative toxicity has ruled out its further use in pools. Quaternary ammonia compounds (QACs), most commonly quaternary ammonia halides, are more effective than copper and not as toxic. Unfortunately, when these compounds react with chlorine, chloramines may be formed which cause eye irritation. QACs will also reduce chlorine levels, increase chlorine demand, collect on filters, and cause pool water to foam, thus having negative effects on water chemistry and clarity. Unfortunately, it has been noted that some algae have developed resistance to QACs.

Linear polymeric biguanides have been disclosed in British Patent 1,407,258 to control the growth of algae and bacteria in swimming pool water. Additionally, British Patent 1,464,005 uses a linear polymeric biguanide as a water treatment for the destruction of aquatic molluscs. The preferred polymeric biguanide for use in both inventions is poly(hexamethylene biguanide) in the form of its hydrochloride salt.

Substituted and branched alkylamines, as in for example, U.S. Pat. No. 4,608,289, and N,N-Dimethylalklamine oxides, for example as discussed by Devinsky et al., (1990, J. Pharm. Pharmacol. 42: 790–794) have been studied for their antimicrobial properties. These substituted and branched alkylamines when incorporated into liquid or molten plastic materials provide fungicidal and bactericidal properties. Examples of plastic materials cited in U.S. Pat. No. 4,608,289 are polyvinyl chloride (PVC), polyethylene, cellulose acetate buterate, polyolefins, polypropylenes, polystyrene, various phenolic resins and polystyrene butadiene.

This invention provides for compounds which are suitable for general use in the treatment of swimming pools, spas, etc and is especially concerned with the treatment of surfaces which tend to become fouled by microorganisms. The addition of this invention to an aquatic environment prevents surface adherence to materials commordy used in swimming pools, spas and the like while keeping the water appearance fresh and clean.

SUMMARY OF THE INVENTION

This invention is a method for treating swimming pools, spas and the like, by providing an effective antimicrobial amount of straight chain alkylamine or their salts to the pool water. Without wishing to be bound by any particular theory of operability, it is believed that a particular benefit of this treatment is that an association is found between the alkylamines and the surfaces of materials commonly used in pools, thereby enhancing antimicrobial effectiveness.

In a distinct embodiment of this invention, the straight chain alkylamines are combined with a second bactericidal agent. Preferred bactericidal agents are biguanides or water soluble biguanide salts of the general formula:

each of *S. marcescens*, *C. Albicans*, and *A. fumigatus*, plotted as Log reduction (CFU/ml) after 4 hour exposure.

DETAILED DESCRIPTION OF THE INVENTION

The disinfecting agent of the instant invention contains a compound selected from the group of straight chain alkylamines, in particular those which comprise a linear alkyl chain having from 6 to 18 carbons, or suitable water-soluble salt thereof. In particular, the invention identifies alkylamines of 13 to 16 carbons as being particularly effective. In contrast to QACs and branched alkylamines, which are easily soluble in water and allow for high concentrations of these compounds in solutions, straight chain alkylamines are not readily soluble at high concentration. The suprising discovery that soluble amounts of the alkylamines of the instant invention were still effective as antimicrobial agents provides new compunds for use in treating pool equipment, surfaces and water. It has been found that typically, solutions of up to 2200 ppm of straight

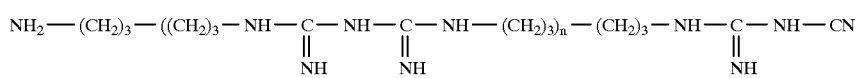

(I)

Figure 1:
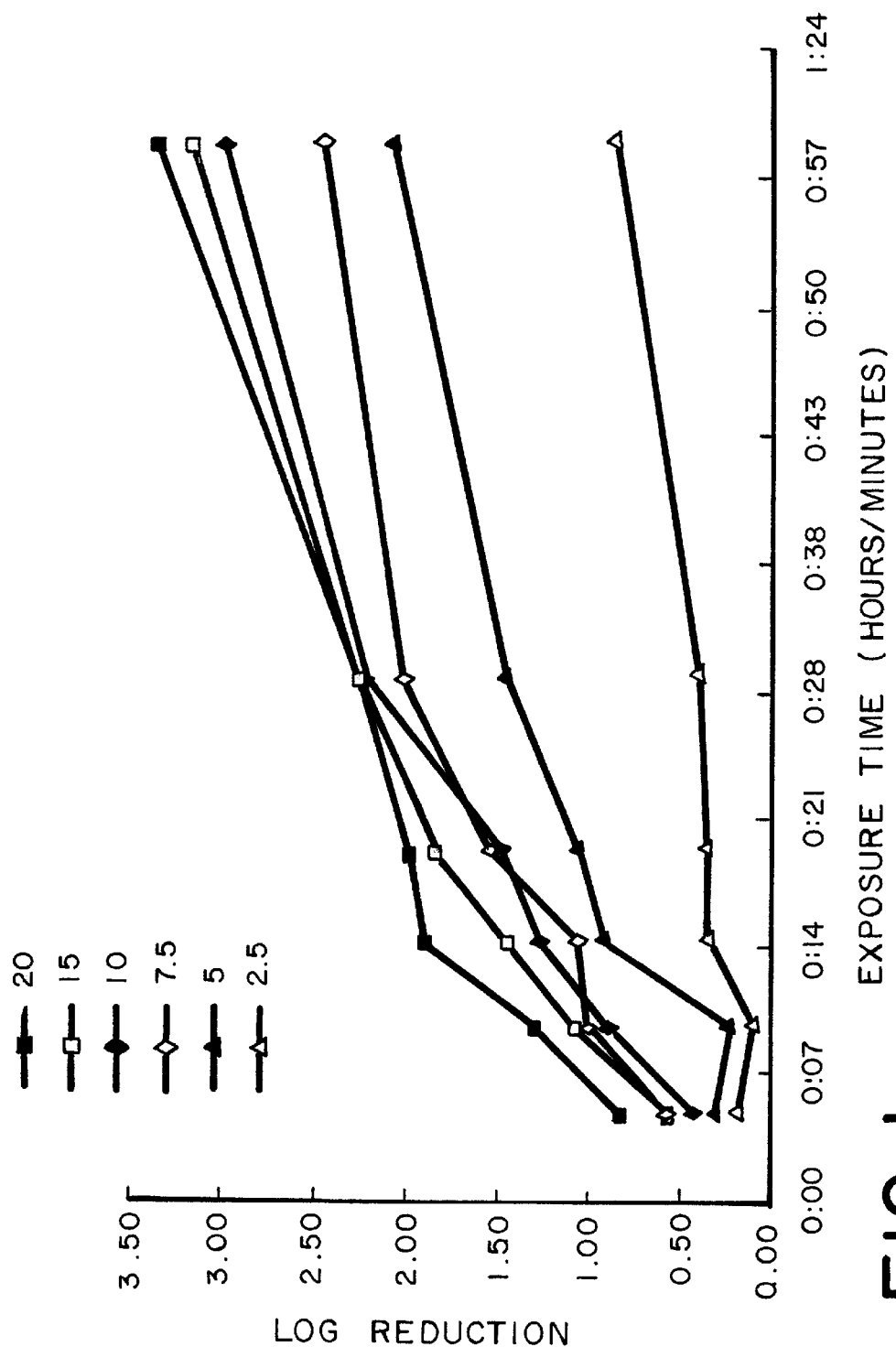
FIG. 1 is a graph showing the effects of tetradecylamine on *A. fumigatus* at various concentrations. The figure plots log reduction in CFU/ml (colony forming units per ml) vs. exposure time (in hours:minutes). Six concentrations of tetradecylamine are shown: at 20 ppm (Solid box); 15 ppm (Open box); 10 ppm (Solid diamond); 7.5 ppm (Open diamond); 5 ppm (Solid triangle); and 2.5 ppm (Open triangle).

The straight chain alkylamine compounds of the methods of the instant invention are particularly suited for treatment and disinfection of pool surfaces and equipment because they show a hydrophobic attraction to many surfaces which enhance their adhesion to such surfaces. Examples of such surfaces include gelatins, resins, and plastics including polystyrene. The effect of such adhesion is to create a long lasting presence of the antimicrobial agent on such surfaces, and to enhance a higher local concentration of antimicrobial agent at such surfaces. The net effect is to enhance the antimicrobial efficacy, and to further inhibit the establishment of microbial attachments to surfaces.

The straight chain alkylamines used in the method of this invention are preferably considered with other antimicrobials agents for the treatment of pool water. A preferred class of agents is biguanides, particularly polyhexamethylene biguanide, (a polymer of hexamethylene biguanide), also referred to as polyaminopropyl biguanide and water-soluble salts thereof (see U.S. Pat. Nos. 4,836,986 and 4,758,595, all hereby incorporated by reference). The biguanides for use in the instant invention (aka. PHMB) include repeating units of the general formula:

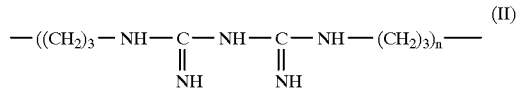

(II)

wherein n is 1 to 500, and include biguanides represented by formula (I) and water soluble salts thereof.

The biguanides for use in the present invention include hexamethylene biguanides, their polymers and water-soluble salts of such base compounds and polymers. Generally, the polymers have molecular weights of up to about 100,000. The antibacterial action of the biguanide-containing solutions described herein may also be supplemented by the addition of other germicidal agents. In a most preferred embodiment the biguanides are a polyhexamethylene biguanide.

The above-disclosed biguanides and methods of preparation are described in the literature. For example, U.S. Pat. No. 3,428,576 (incorporated by reference) describes the preparation of such biguanides from a diamine and salts thereof and a diamine salt of dicyanimide. This patent expressly teaches methods of making, e.g., the hydrochloride salt of polyhexamethylene biguanide which is also commercially availible from ICI Americas, Inc., Wilmington, Del. 19897, under the trademark Cosmocil CQ. For convenience purposes only, the biguanides described hereinafter shall be referred to as "PHMB" where the specific species polyhexamethylene biguanide is referred to as "PAPB".

Preferred polyhexamethylene biguanides include lower molecular weight oligomers, including biguanides of formulae (I and I) wherein n averages between 1 to 500, more preferably 2 to 12 and most preferably 3 to 8. A more preferred material is the polyhexamethylene biguanide hydrochloride available under the trademark name Cosmocil CQ (ICI Americas, Inc., Wilmington, Del., USA).

Applicants have discovered that the antimicrobial system of this invention provides desired antibacterial efficacy with relatively low amounts of polyhexamethylene biguanide, and specifically enhanced antifungal and antimicrobial efficacy by using straight chain alkylamines of the instant invention, thus providing an effective antimicrobial composition with minimal potential for adverse effects such as eye irritation which is particularly suitable for use in the methods of the instant invention as applied to surfaces. Thus the instant invention provides for methods of treating pool surfaces with disinfecting agents in which the components are provided in an antimicrobially effective amount. An antimicrobially effective amount is an amount which is effective to at least inhibit the growth of microorganisms on a surface that has been treated, or in a solution that has been treated.

To combat the growth of microorganisms, it has been found that the resulting pool water preferably contains from about 0.001 ppm (parts per million) by weight to about 2200 ppm straight chain alkylamine components, more preferably, 1 ppm by weight to 2200 ppm by weight straight chain alkylamines of 6 to 18 carbons, still more preferably 5 to 500 ppm by weight straight chain alkylamines of 11 to 16 carbons and most preferably 5 to 25 ppm by weight straight chain alkylamines of 13 to 15 carbons.

As mentioned the straight chain alkylamine are preferably used with an additional antimicrobial, the preferred being a polymeric biguanide or its salt. The more preferred of the biguanides is polyhexymethylene biguanide or its salt and the most preferred of the biguanides is polyhexamethylene biguanide hydrochloride. The pool water should contain I ppm by weight to about 200 ppm by weight of the poly-hexamethylene biguanide component, more preferably 1 ppm by weight to about 100 ppm and most preferably about 30 to 70 ppm. In the preferred embodiment, the swimming pool water should contain a straight chain alkylamine and a polmeric biguanide.

Although optimum amounts of the specific antimicrobial agents may vary according to specific applications, the specific amounts and the need for additional components can be readily determined by one of ordinary skill in the art following testing methods known in the art. The following examples further illustrate preferred embodiments of the present invention.

EXAMPLE 1

ANTIMICROBIAL EFFICACY

The graph of FIG. 1 depicts data from an experiment demonstrating the effects of tetradecylamine concentration on *A. fumigatus*, one of the most common fungi in the human environment. The graph plots log reduction in microorganisms versus exposure time in minutes for concentrations of tetradecylamine ranging from 2.5 ppm up to 20 ppm. The results are plotted as log reduction in colony forming units per ml (CFU/ml) against exposure time, for the various concentrations.

Figure 2:
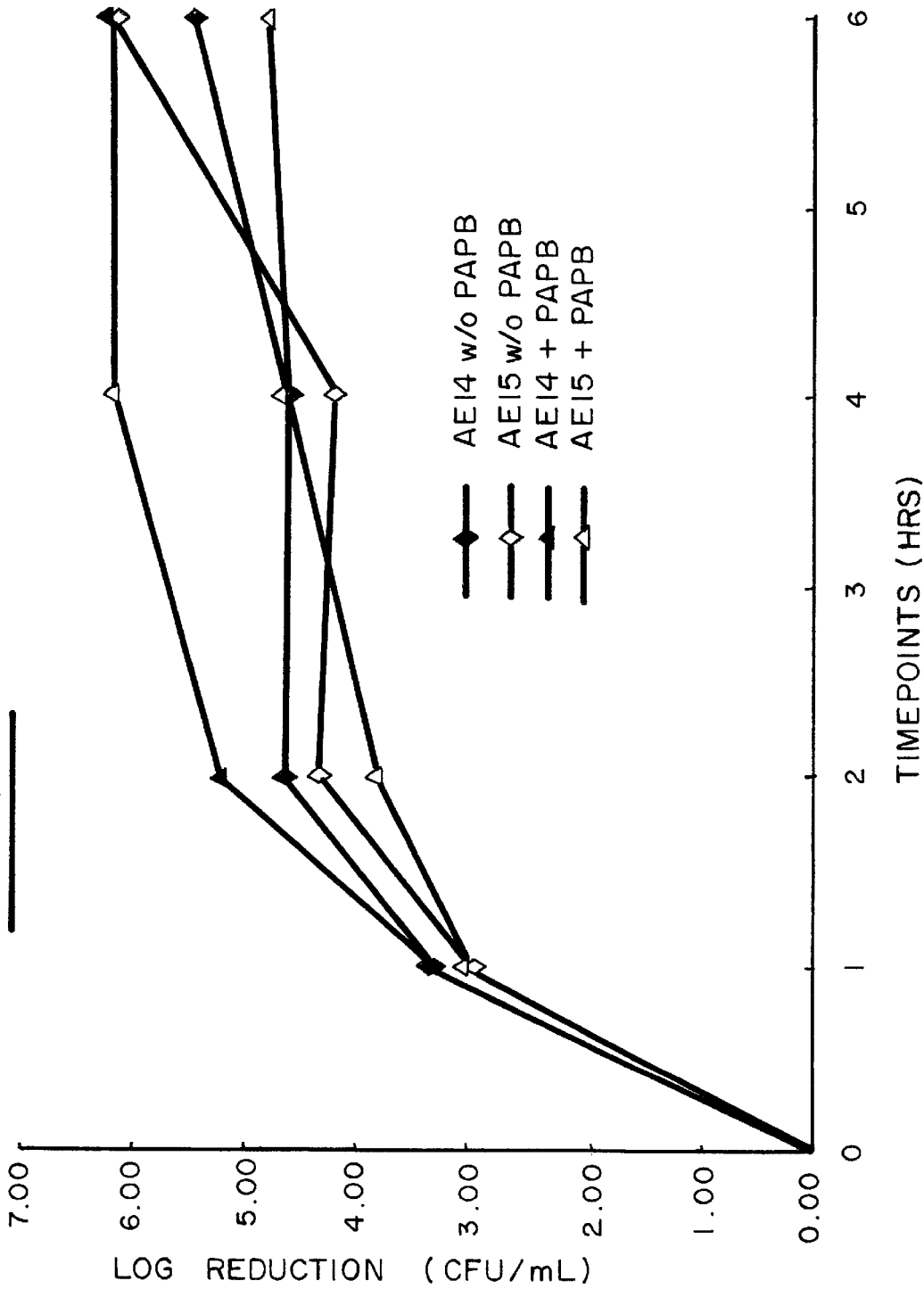
FIG. 2 shows biocidal efficacy of tetradecylamine and pentadecylamine on *S. marcescens* by plotting log reduction (as CFU/ml) against time of exposure (in hours). Compositions shown are: tetradecylamine (10 ppm) without polyhexamethylene biguanide (Solid diamond); pentadecylamine (10 ppm) without polyhexamethylene biguanide (Open diamond); tetradecylamine (10 ppm) with polyhexamethylene biguanide (0.8 ppm) (Solid triangle); and pentadecylamine (10 ppm) with polyhexamethylene biguanide (0.8 ppm) (Open triangle).

FIG. 2 depicts data from an experiment demonstrating the efficacy of tetradecylamine and pentadecylamine on *S. marcescens*, a gram-negative bacilli considered more resistant to antimicrobials than *Escherichia coli*. In addition to the straight chain alkylamine, added polyhexamethylene biguanide was tested. The efficacy of a standard solution containing 0.8 ppm polyhexamethylene biguanide and 10 ppm tetradecylamine or pentadecylamine, HCl, was compared with solutions without polyhexamethylene biguanide. The graph plots log reduction (in CFU/ml) versus time of exposure (in hours).

Figure 3:
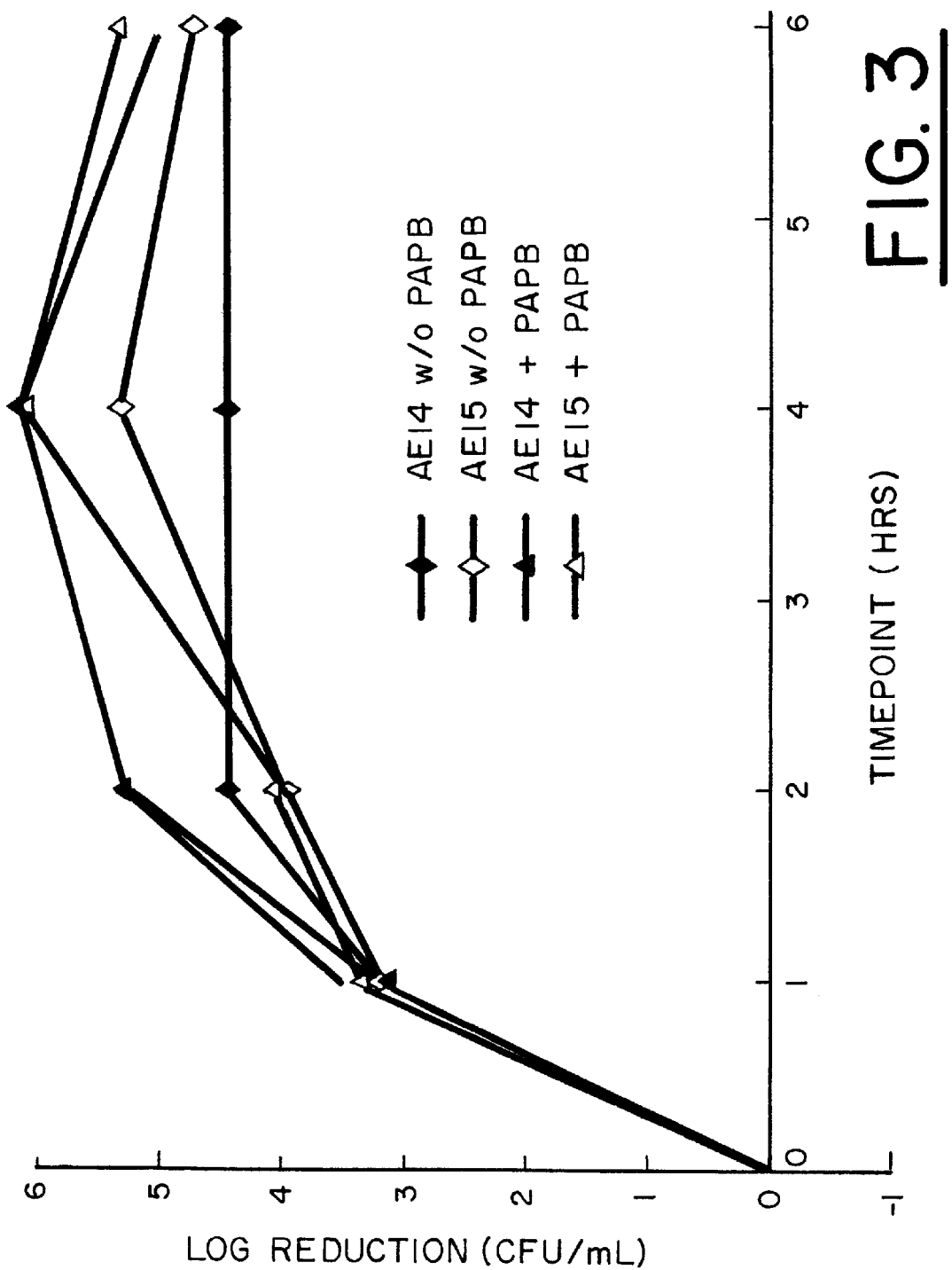
FIG. 3 shows biocidal efficacy of tetradecylamine and pentadecylamine on *C. albicans* by plotting log reduction (as CFU/ml) against time of exposure (in hours). Compositions shown are: tetradecylamine (10 ppm) without polyhexamethylene biguanide (Solid diamond); pentadecylamine (10 ppm) without polyhexamethylene biguanide (Open diamond); tetradecylamine (10 ppm) with polyhexamethylene biguanide (0.8 ppm) (Solid triangle); and pentadecylamine (10 ppm) with polyhexamethylene biguanide (0.8 ppm) (Open triangle).

FIG. 3 depicts data from an experiment demonstrating the efficacy of tetradecylamine and pentadecylamine on *C. albicans*, a ubiquitous, usually saprophytic yeast. In addition to the straight chain alkylamine, an excipient, and added polyhexamethylene biguanide was tested. The efficacy of a standard solution containing 0.8 ppm polyhexamethylene biguanide and 10 ppm tetradecylamine or pentadecylamine, HCl, was compared with solutions without polyhexamethylene biguanide. The graph plots log reduction (in CFU/ml) versus time of exposure (in hours).

Figure 4:
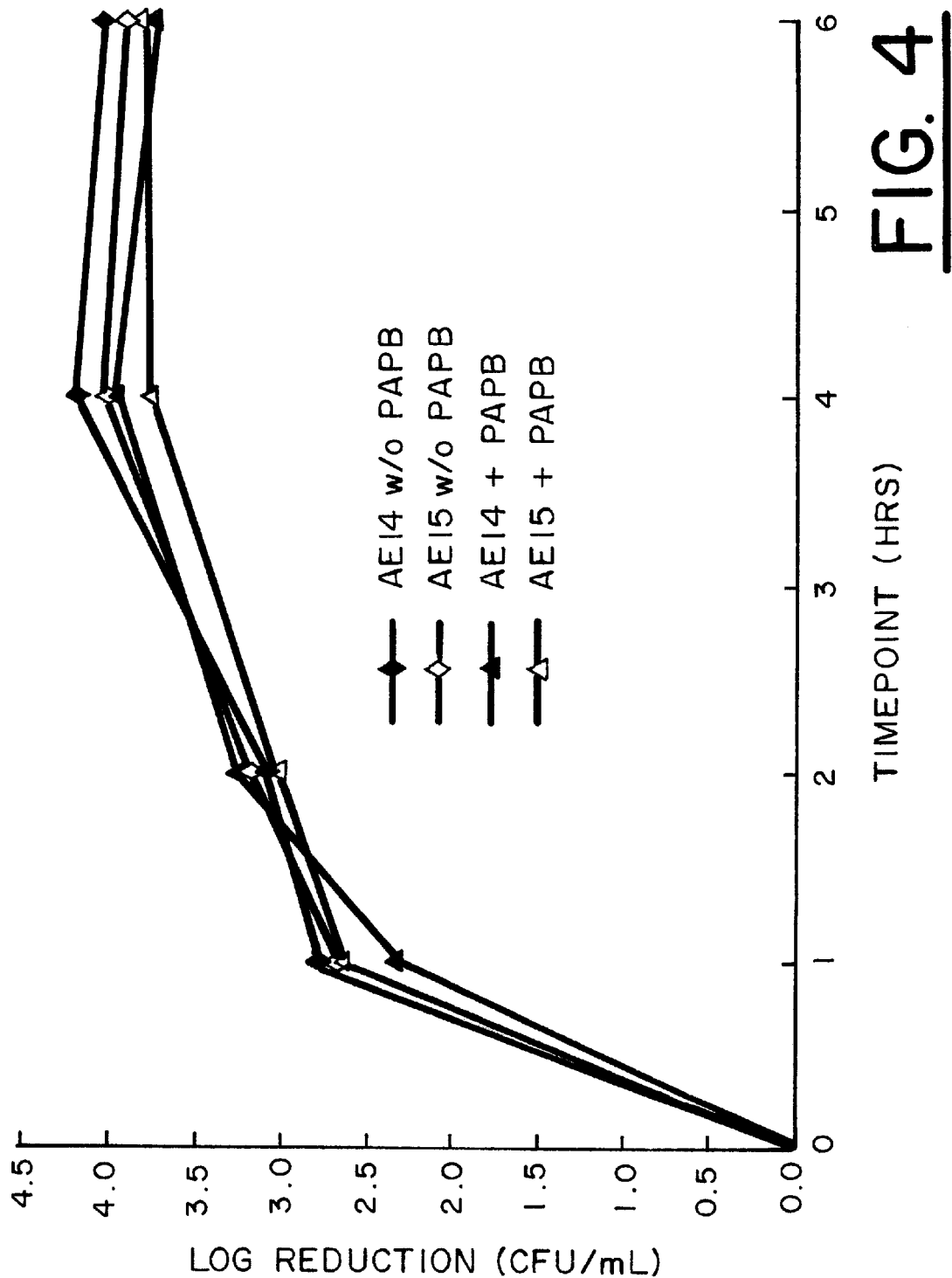
FIG. 4 shows biocidal efficacy of tetradecylamine and pentadecylamine on *A. fumigatus* by plotting log reduction (as CFU/ml) against time of exposure (in hours). Compositions shown are: tetradecylamine (10 ppm) without PAPB (Solid diamond); pentadecylamine (10 ppm) without PAPB (Open diamond); tetradecylamine (10 ppm) with polyhexamethylene biguanide (0.8 ppm) (Solid triangle); and pentadecylamine (10 ppm) with polyhexamethylene biguanide (0.8 ppm) (Open triangle).

FIG. 4 depicts data from an experiment demonstrating the efficacy of tetradecylamine and pentadecylamine on *A. fumigatus*. In addition to the straight chain alkylamine, polyhexamethylene biguanide was tested. The efficacy of a standard solution containing 0.8 ppm polyhexamethylene biguanide and 10 ppm tetradecylamine or pentadecylamine, HCl, was compared with solutions without polyhexamethylene biguanide. The graph plots log reduction (in CFU/ml) versus time of exposure (in hours).

The data clearly show that straight chain alkylamines, either alone or in combination with other bactericidal agents are effective in inhibiting microbial growth. Thus the compunds of the invention are useful antimicrobial agents which will be most suitable for use in methods to disinfect and treat pool surfaces and equipment.

COMPARATIVE EXAMPLE A

The antimicrobial efficacy of various branched N,N Dimethyl alkylamines where the length of the alkylamines ranged from 10 to 18 carbons demonstrated almost no efficacy as measured as log reductions (CFU/ml) against *S. marcescens, C. albicans,* and *A. fmigatus*. The effect measured was on the order of 0.3 to 0.1 (CFU/ml) reduction at 1 hour, and from a reduction of 0.6 to and increase in growth after 4 hours.

EXAMPLE 2

COMPARATIVE ANTIMICROBIAL EFFICACY

Direct comparisions of the effect of varying the length of the carbon chains of the alkylamines on antimicrobial efficacy were performed.

Figure 5:
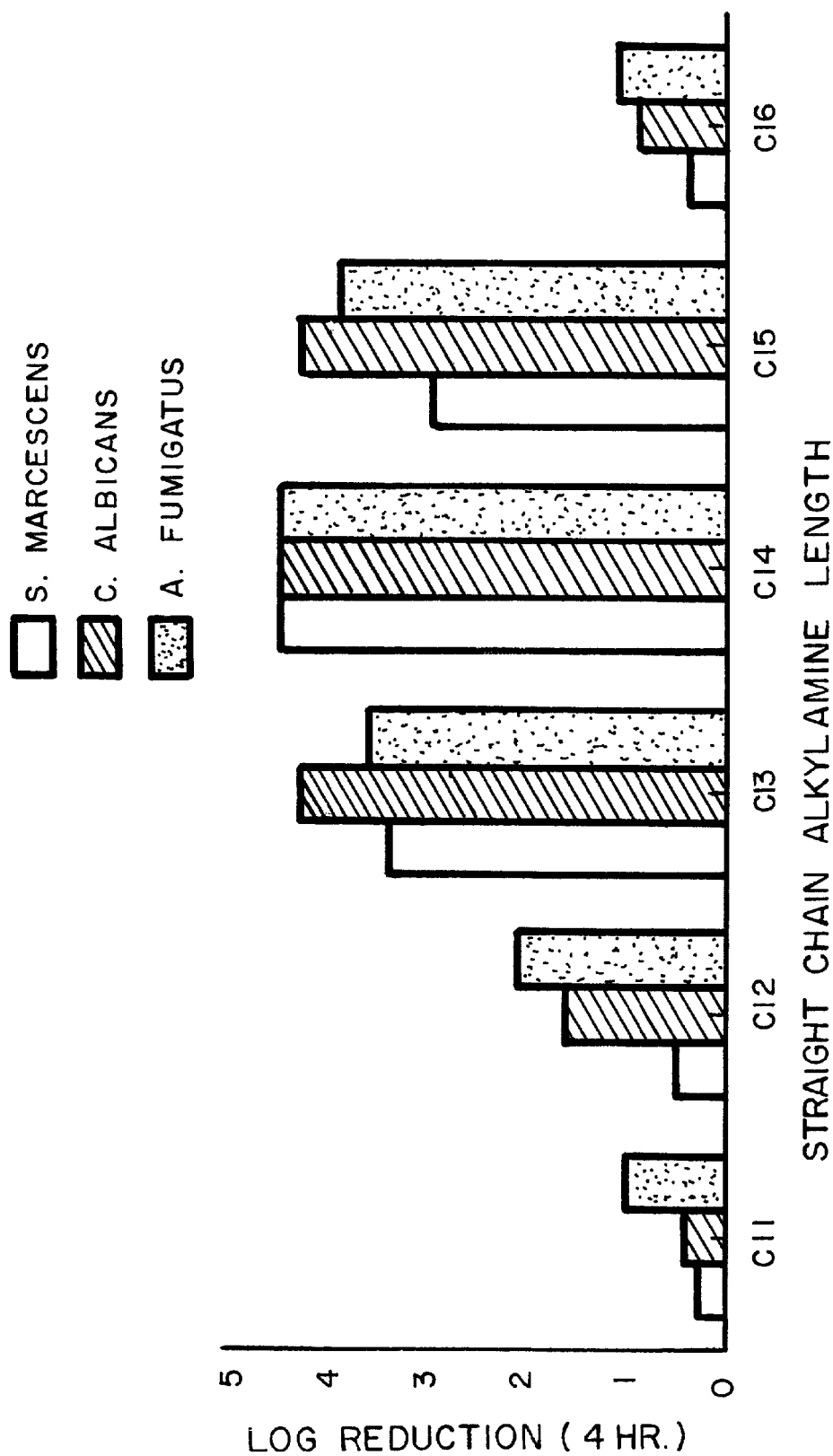
FIG. 5 is a comparison of the effect of alkylamine chain length (at 10 ppm in borate buffer) on the efficacy against chain alkylamines of 6 to 18 carbons can be formed. In a more preferred embodiment, the straight chain alkyl amine is provided as its hydrochloride salt.

FIG. 5 shows results of varying alkyamine chain length on cytotoxicity versus *S. marcescens, C. albicans,* and *A. fumigatus*. Data is graphed as log reduction [CFU/ml] after 4 hours exposure, and all alkylamines were tested at 10 ppm in Borate buffer. The data clearly shows that while effective killing was present at chain lengths of 11 through 16 carbons, the most effective compositions were alkylamines with chain lengths of 13, 14 or 15 carbons.

EXAMPLE 3

ENCAPSULATED ANTIMICROBIAL EFFICACY

It was found that the alkylamines of the instant invention were particularly well suited for topical application to surfaces because of the strong binding of the compounds with hydrophobic surfaces. Attempts to counter such binding with encapsulating agents such as cyclodextrin (gamma-cyclodextrin=CN-3; hydroxypropyl beta-cyclodextrin=CN-9) were deleterious to the antimicrobial efficacy of the compounds. It was found that the best formulation of alkylamines is one which does not inhibit the binding of the compounds with appropriate surfaces or targets. Results showed that in general less CN-9 is better than higher, and no CN-3 is better than any.

Table 1 presents data depicting the efficacy of tetradecylamine at 5 ppm and 7 ppm, in combination with varying amounts of cyclodextrins. In this assay, measurements were taken at 4 and 6 hours and plotted against the log reduction of CFU/ml of *A. fumigatus*. These results are particularly illustrative of the effects on anti-fungal efficacy of the alkylamines when they are combined with agents to reduce certain hydrophobic binding interactions. Thus the data show that the compositions of the instant invention show efficacy for use in methods to disinfect pool surfaces and equipment, and can be modifided to alter the hydrophobicity of their interactions.

TABLE 1

| | Log Reduction of *A. fumigatus* | |
|---|---|---|
| | 4 hour | 6 hour |
| 5 ppm C14 + 0.01% CN9 | 1.3 | 1.2 |
| 5 ppm C14 + 0.025% CN9 | 0.6 | 0.2 |
| 5 ppm C14 + 0.05% CN9 | 0.2 | 0.2 |
| 7 ppm C14 + 0.01% CN9 | 1.6 | 2.2 |
| 7 ppm C14 + 0.25% CN9 | 0.5 | 0.9 |
| 7 ppm C14 + 0.05% CN9 | 0.0 | 0.4 |

The invention may be embodied in other forms or carried out in other ways without departing from the spirit or essential characteristics thereof The present disclosure is therefore to be considered as in all respects illustrative and not restrictive, the scope of the invention being indicated by the appended Claims, and all equivalency are intended to be embraced therein, the scope of the invention being indicated by the appended claims, and all changes which come within the meaning and range of equivalency are intended to be embraced therein. One of ordinary skill in the art would be able to recognize equivalent embodiments of the instant invention, and be able to practice such embodiments using the teaching of the instant disclosure and only routine experimentation.

What we claim is:

1. A method for treating swimming pools and spas comprising contacting surfaces, pool water, or equipment with a solution having an effective antimicrobial amount of straight chain alkylamine or salt thereof having 13 to 15 carbon atoms.

2. The method of claim 1 where in addition there is an effective antimicrobial amount of a bactericidal agent.

3. The method of claim 2 where the additional bactericidal agent is a biguanide or its water-soluble salt having the general repeating formula:

$$-((CH_2)_3-NH-\underset{\underset{NH}{\|}}{C}-NH-\underset{\underset{NH}{\|}}{C}-NH-(CH_2)_3)_n- \qquad (II)$$

where n=1 to 500.

4. A method of claim 3 where the composition contains from about 1 ppm by weight to about 200 ppm by weight of a polyhexamethylene biguanide component or its water-soluble salt.

5. A method of claim 3 where the composition also contains at least about 1 ppm by weight to about 100 ppm by weight of a polyhexamethylene biguanide component or its water-soluble salt.

6. A method of claim 3 where the composition also contains at least about 30 ppm by weight to about 70 ppm by weight of a polyhexamethylene biguanide component or its water-soluble salt.

7. A method of claim 3 where the composition contains about 5 ppm by weight to about 25 ppm by weight of a straight chain alkylamine and about 30 ppm by weight to about 70 ppm by weight of a polyhexamethylene biguanide or its water-soluble salt.

8. A method of claim 1 where the composition has about 0.001 ppm by weight to about 2200 ppm by weight of straight chain alkylamines.

9. A method of claim 1 where the composition contains from about 5 ppm by weight to about 500 ppm by weight of straight chain alkylamines.

10. A method of claim 1 where the composition contains from about 5 ppm by weight to about 25 ppm by weight of straight chain alkylamines.

11. A method for treating swimming pools and spas comprising contacting surfaces, pool water, or equipment with a solution having about 0.001 ppm by weight to about 2200 ppm by weight of a straight chain alkylamine having 13 to 15 carbons or salt thereof and about 1 ppm by weight to about 200 ppm by weight a biguanide or its water-soluble salt having the general repeating formula:

$$-((CH_2)_3-NH-\underset{\underset{NH}{\|}}{C}-NH-\underset{\underset{NH}{\|}}{C}-NH-(CH_2)_3)_n- \qquad (II)$$

where n=1 to 500.

12. A method for treating swimming pools and spas comprising contacting surfaces, pool water, or equipment with a solution having about 5 ppm by weight to about 500 ppm by weight of a straight chain alkylamine having 13 to 15 carbons or salt thereof and about 1 ppm by weight to about 100 ppm by weight of a polyhexamethylene biguanide compound or its water-soluble salt.

13. A method for treating swimming pools and spas comprising contacting surfaces, pool water, or equipment with a solution having about 5 ppm by weight to about 25 ppm by weight of a straight chain alkylamine having 13 to 15 carbons or salt thereof and about 30 ppm by weight to about 70 ppm by weight a polyhexamethylene biguanide compound or its water-soluble salt.

* * * * *